United States Patent [19]

Palmer et al.

[11] Patent Number: 5,722,422
[45] Date of Patent: Mar. 3, 1998

[54] ENDOSCOPIC BIOPSY FORCEPS HANDLE WITH REMOVABLE SAMPLE REMOVAL PICK

[75] Inventors: Matthew A. Palmer, Miami; Peter Kratsch, Sunrise, both of Fla.

[73] Assignee: Symbiosis Corporation, Miami, Fla.

[21] Appl. No.: 799,508

[22] Filed: Feb. 12, 1997

[51] Int. Cl.⁶ .................................................. A61B 10/00
[52] U.S. Cl. ........................................................ 128/751
[58] Field of Search .............................. 128/751; 606/205, 606/206, 207, 131, 170

[56] References Cited

U.S. PATENT DOCUMENTS

| | | | |
|---|---|---|---|
| 5,395,313 | 3/1995 | Naves et al. | 128/751 |
| 5,454,378 | 10/1995 | Palmer et al. | 128/751 |

Primary Examiner—Michael Buiz
Assistant Examiner—Kevin Truong

Attorney, Agent, or Firm—Finnegan, Henderson, Farabow, Garrett & Dunner, L.L.P.

[57] ABSTRACT

An endoscopic biopsy forceps instrument includes an actuation handle having a stationary member coupled to a movable member, a tubular member coupled at its proximal end to the stationary member, a control wire extending through the tubular member and coupled at its proximal end to the movable member, and a biopsy forceps jaw assembly having jaw cups. The jaw assembly is coupled to the distal ends of the tubular member and control wire, such that movement of the movable member relative to the stationary member imparts relative movement of the control wire relative to the tubular member and opens and closes the jaws. The distal end of the stationary member includes a groove for holding a sample removal pick. A sample removal pick shaped to be slidably engaged in the holder is received within the holder. The pick may include catches and ridges for engagement by a human finger, such that the catches and ridges may be engaged by the practitioner to slide the pick out of the holder. The pick can then be used to remove tissue samples lodged within the jaw cups of the jaw assembly.

20 Claims, 10 Drawing Sheets

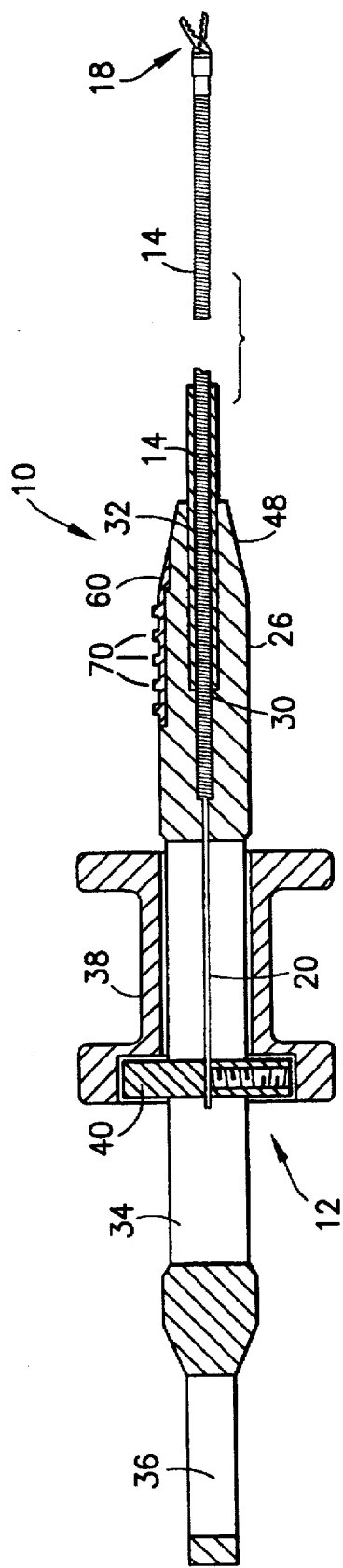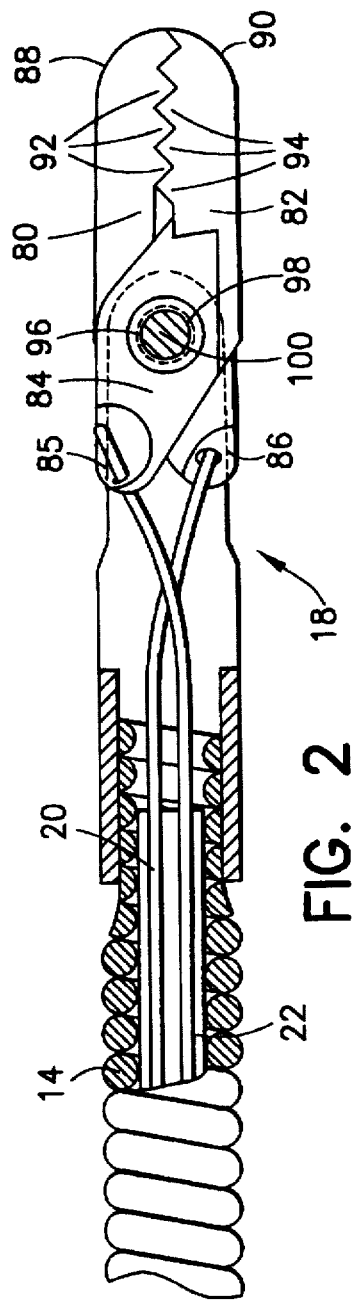

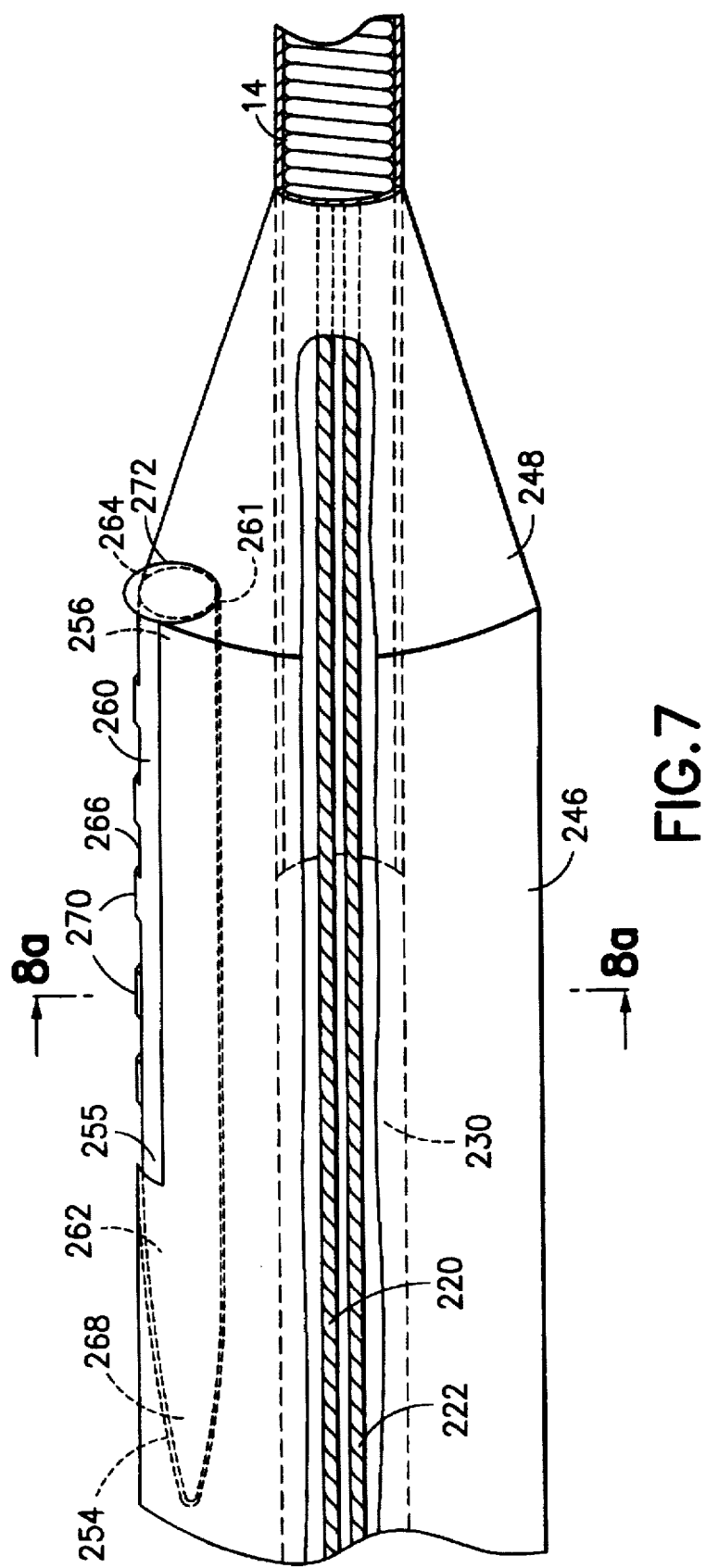

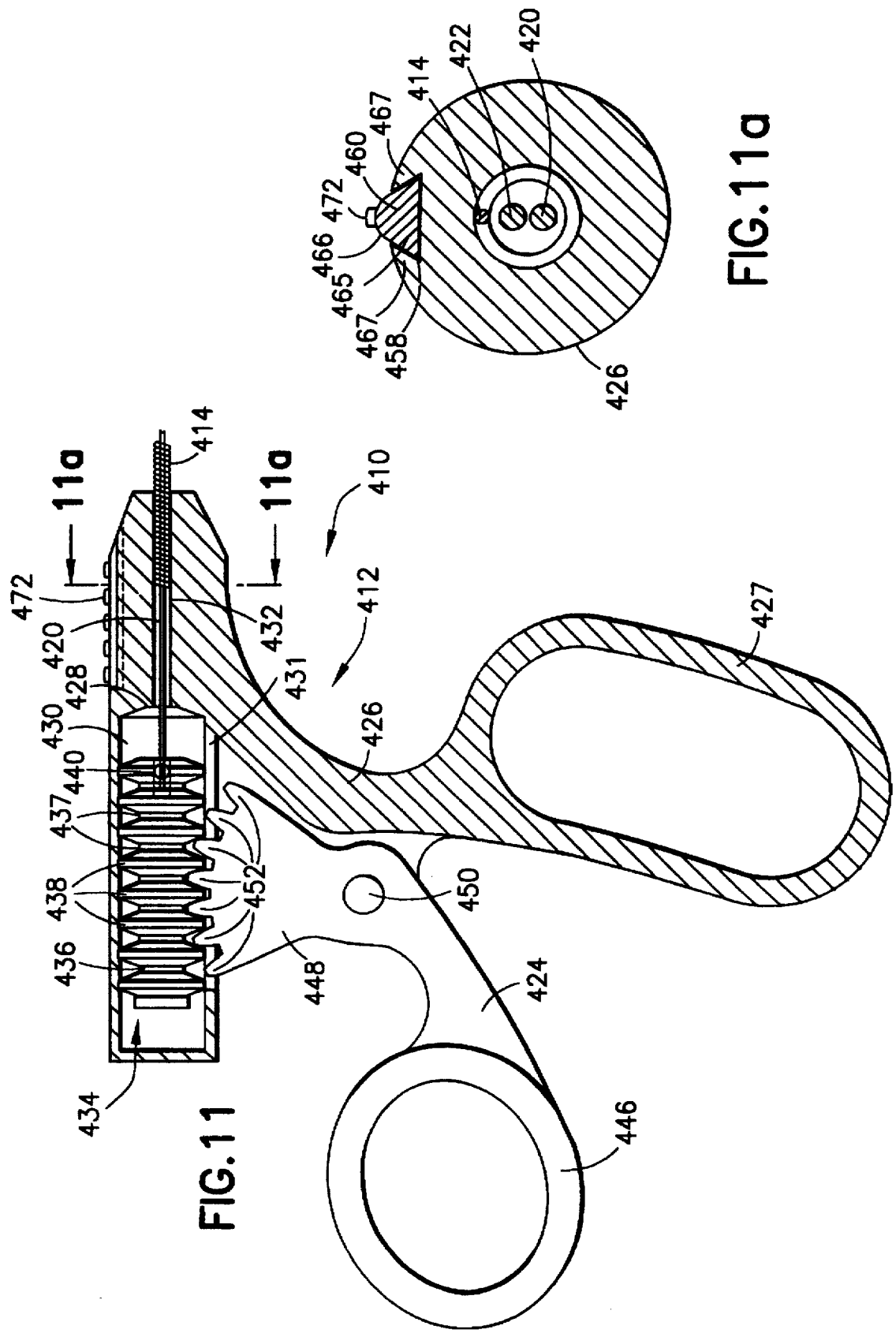

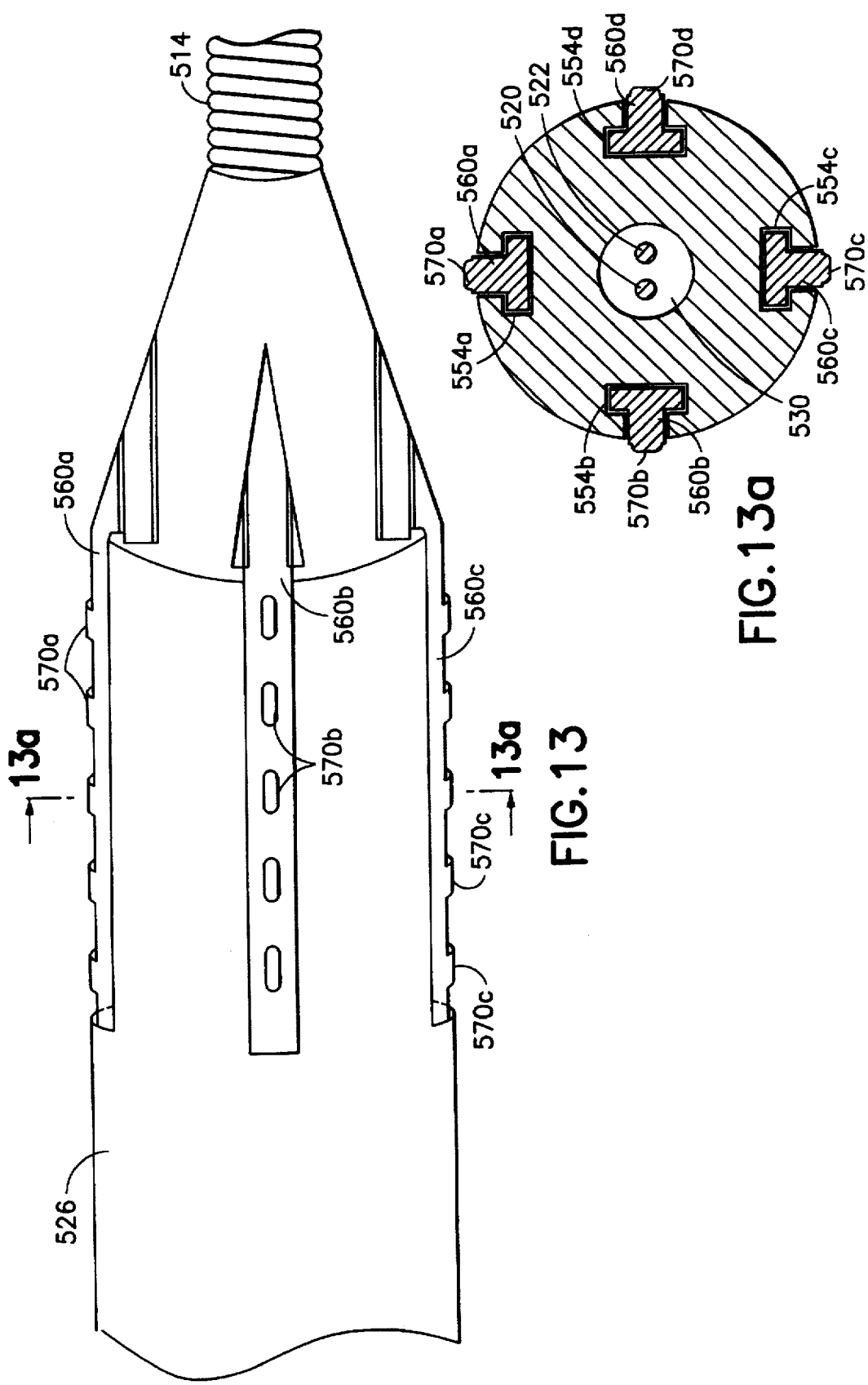

ENDOSCOPIC BIOPSY FORCEPS HANDLE WITH REMOVABLE SAMPLE REMOVAL PICK

This application is related to co-owned U.S. Pat. No. 5,228,451, entitled "Biopsy Forceps Device Having Stiff Distal End" and co-owned U.S. Pat. No. 5,478,350, entitled "Rack and Pinion Actuation Handle For Endoscopic instruments" which are hereby incorporated by reference herein in their entireties.

BACKGROUND OF THE INVENTION

1. Field of the Invention

This invention relates broadly to endoscopic surgical instruments. More particularly, this invention relates to endoscopic biopsy forceps instruments and picks for retrieving biopsy specimens from the jaws of the forceps instrument.

2. State of the Art

Endoscopic biopsy forceps instruments generally include an actuation handle and a long coil coupling the handle to a pair of forceps jaws. A control wire extends through the coil and is coupled at its proximal end to a movable part of the handle and at its distal end to the forceps jaws. Movement of the control wire relative to the coil opens and closes the forceps jaws. The forceps jaws are cup shaped and extremely small, typically 2 to 4 millimeters in overall diameter.

In general, an endoscopic biopsy procedure involves the use of a camera or magnifying lens inserted through a lumen of an endoscope. The distal end of the biopsy forceps instrument is inserted through another lumen of the endoscope with the biopsy forceps jaws in a closed position. The jaws are maneuvered to the desired location and the actuation handle is used to open the biopsy forceps jaws. The jaws are brought toward the tissue to be sampled, and the actuation handle is used to close the jaws on and sever a tissue sample, trapping a tissue sample within the jaw cups. The biopsy forceps are removed from the endoscope with the jaws closed. The specimen or sample must then be recovered from the jaws of the forceps. Due to the small size of the jaws and the nature of the tissue sample, the sample often cannot be dislodged from the jaw cups by merely tapping the jaws on the side of a specimen container. Furthermore, tapping may cause the small sample to dislodge outside the specimen container, resulting in a lost or contaminated sample. As a result, the samples must be manually removed. One method for manually removing the sample out of the biopsy forceps jaws is to use a tool such as a sample removal pick. However, picks and other removal tools are small and are often misplaced.

It is important that a tool for sample removal be always available. Moreover, it is important that the person recovering the sample have convenient access to the tool so that the sample may be recovered with little opportunity for the sample to become contaminated.

SUMMARY OF THE INVENTION

It is therefore an object of the invention to provide an endoscopic biopsy forceps instrument incorporating therein a tool for removing a biopsy sample from the forceps jaws.

It is another object to provide an endoscopic biopsy forceps instrument with a handle having a removable tool which is held securely by the handle.

It is a further object to provide an endoscopic biopsy forceps handle having a removable pick which is easily removable from the handle.

In accord with these objects which will be discussed in detail below, an actuator handle assembly is provided for an endoscopic biopsy forceps instrument with a pick holder slot or pick holder bore for removably receiving a sample removing pick. A sample removal pick is frictionally engaged in the holder. In one embodiment, the sample removal pick is trapezoidal-shaped. In another embodiment the pick is T-shaped. In yet other embodiments the pick is cylindrical or conical. In each embodiment the pick holder is shaped to frictionally engage the pick. Furthermore, in some embodiments, the pick has ridges on its back which enable a practitioner's finger to frictionally engage the pick and to slide the pick distally out of the holder. In other embodiments the pick has a finger catch at a manipulation end for engagement by a finger. Furthermore, an embodiment is disclosed in which multiple picks are removably engaged in multiple pick holding slots or bores in the actuator handle assembly.

An endoscopic biopsy forceps instrument incorporating the handle assembly of the invention is also disclosed. The forceps instrument includes a tubular member, a control member, and a pair of biopsy forceps jaws. The control member extends through the tubular member and both the control member and the tubular member are coupled at their proximal ends to the actuator handle and at their distal and to the biopsy forceps jaws, such that actuation of the actuation handle causes relative movement of the control member and the tubular member and results in the opening and closing of the forceps jaws.

With the above embodiments it will be appreciated that after obtaining a sample and removing the forceps instrument from the endoscope, the pick is slidably removed from the actuator handle assembly by engaging a finger at either the ridges on the back of the pick or at the finger catch of the pick. The pick can then be manipulated to manually remove the tissue sample from the biopsy forceps jaw cups and to deposit the sample into a container for later evaluation. After the pick deposits the sample into a container, the handle and pick can either be disposed of or sterilized for future use.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of a first embodiment of a biopsy forceps instrument according to the invention;

FIG. 2 is an enlarged broken side elevation view in partial section of the distal end of the biopsy forceps instrument of FIG. 1;

FIG. 7 is a view similar to FIG. 3 of a third embodiment of the invention;

FIG. 11 is a broken side elevation view in partial section of a fifth embodiment of the invention;

FIG. 11a is a cross-section along line 11a—11a;

FIG. 13 is a side elevation view in partial section of a sixth embodiment of the invention; and FIG. 13a is a cross-section along line 13a—13a.

DETAILED DESCRIPTION OF THE PREFERRED EMBODIMENTS

Figure 3:
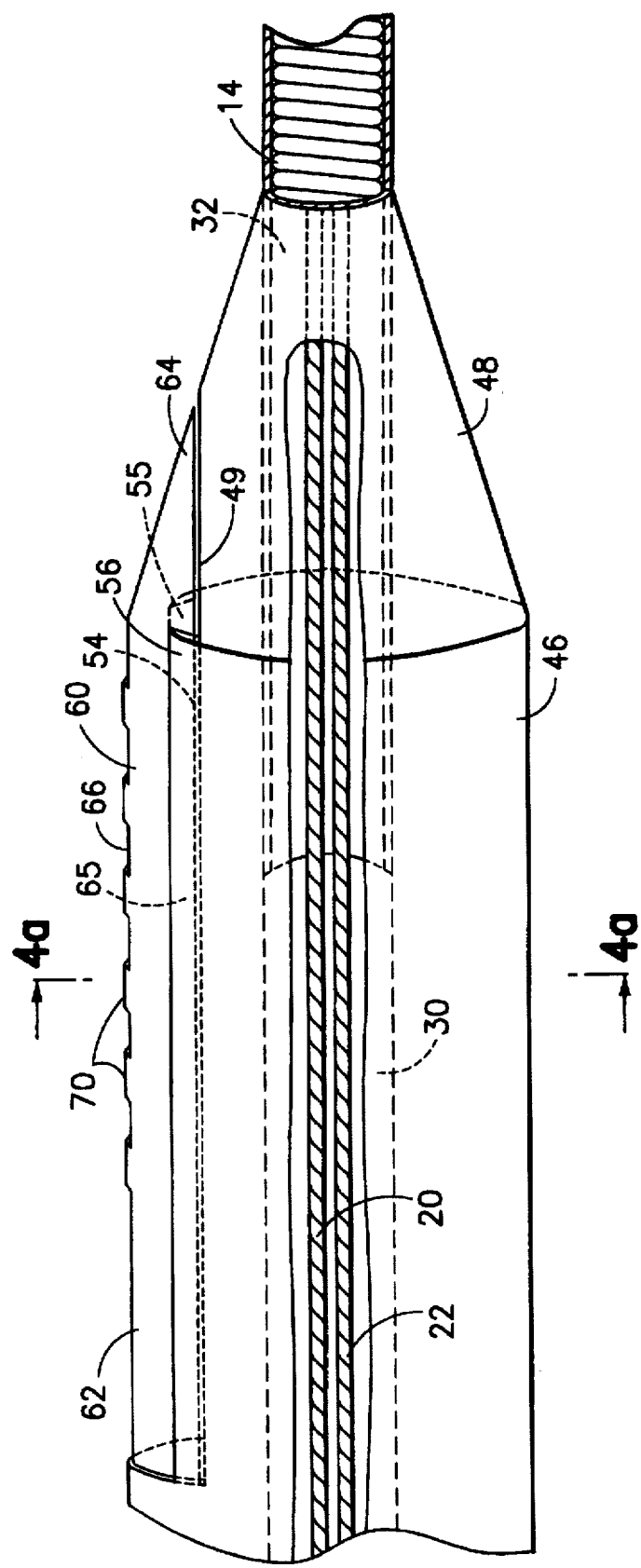
FIG. 3 is an enlarged broken side elevation view in partial section of the instrument of FIG. 1.

Referring generally to FIGS. 1 and 2, a first embodiment of an endoscopic biopsy forceps instrument 10 includes an actuation handle 12, a coil 14, biopsy forceps end effectors 18, and control wires 20, 22. As shown in FIG. 1, the actuation handle 12 typically includes a stationary member 26 and a displaceable spool 38. The stationary member includes a distal throughbore 30, a central slot 34, and a proximal thumb ring 36. The displaceable spool 38 is slidably disposed on the stationary member 26 and has a cross member 40 which passes through the slot 34. The proximal ends of the control wires 20, 22 are coupled to the cross member 40 of the spool 38. Operation of the actuation handle is described fully in co-owned U.S. Pat. No. 5,228,451.

The end effector 18 shown in FIG. 2 generally includes a pair of identical jaws 80, 82 having jaw cups 88, 90 and a clevis 84. Each jaw 80, 82 has a proximal tang 85, 86, a jaw cup 88, 90 having teeth 92, 94, and a transverse bore 96, 98. The control wires 20, 22 extend through the flexible coil 14 and the proximal tangs 85, 86 of the jaws 80, 82 are coupled to the ends of the control wires 20, 22. The jaws 80, 82 are attached to the clevis 84 by a clevis pin 100 which passes through the transverse bore 96, 98 of each jaw 80, 82. Operation of the forceps end effector is described in detail in co-owned U.S. Pat. No. 5,228,451 to Bales et al.

The coil 14 extends over the control wires 20, 22 and the proximal end of the coil is coupled to the actuation handle 12 and the distal end of the coil is coupled to the clevis 84. Those skilled in the art will appreciate that movement of the spool 38 relative to the stationary member 26 effects a translational movement of the control wires 20, 22 relative to the coil 14 and opens and closes the jaws 80, 82.

Figure 4A:
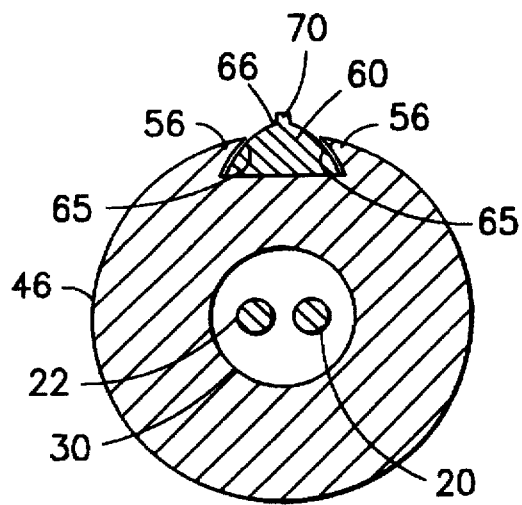
FIG. 4a is a cross-section taken along line 4a—4a in FIG. 3.
Figure 4B:
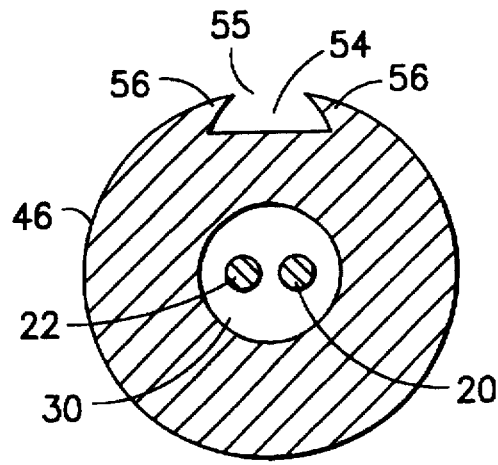
FIG. 4b is a view similar to 4a with the pick removed.

As seen best in FIGS. 3 and 4b, the distal portion 46 of the stationary member 26 is substantially cylindrical and has a substantially frustoconical portion 48. In accord with the invention, a pick holder 54 is provided in the stationary member 26. The holder 54 is a cutout in the stationary member having an entrance at a frustoconical portion 48 of the stationary member and extending proximally into the distal cylindrical portion 46 of the stationary member. The holder is substantially trapezoidal in profile with an open slot portion 55 and two wings 56. A pick 60 with a dovetail or trapezoidal cross-section has a proximal end 62, a distal arrow-shaped tip 64, sides 65, and a back 66. The pick 60 is slidably engaged in the holder 54 (FIG. 4a) with the open slot 55 of the holder 54 exposing the back 66 of the pick, and the wings 56 frictionally engaging the sides 65 of the pick. The arrow-shaped distal tip 64 rests on a flattened portion 49 of the frustoconical portion 48 of the stationary member 26. The back 66 of the pick preferably has several ridges 70 engageable by a practitioner's finger so that pressure may be applied to the ridges to overcome friction and slide the pick 60 out of the entrance at the frustoconical portion 48 of the stationary member 26.

With the above embodiment it will be appreciated that the pick 60 is slidably and frictionally engaged in the holder 54 by aligning the proximal end 62 of the pick 60 with the holder 54 and sliding the pick proximally into the holder. Likewise, the pick 60 is slidably and frictionally disengaged from the stationary member 26 by applying pressure to the ridges 70 with a finger and sliding the pick 60 distally.

In practice, when the forceps end effector 18 of the forceps instrument 10 is removed from an endoscope with a tissue sample caught in the jaw cups 88, 90, the pick 60 is removed from the handle assembly 12. The handle assembly 12 is then actuated to open the jaw cups, and the pick is used to manually remove the tissue sample from teeth 92, 94 of the biopsy forceps jaws 80, 82 and to deposit the sample in a container (not shown) for later evaluation. In the case of a non-disposable instrument, the pick can be cleaned, sterilized and replaced in the handle or a new pick can be placed in the handle.

Figure 6A:
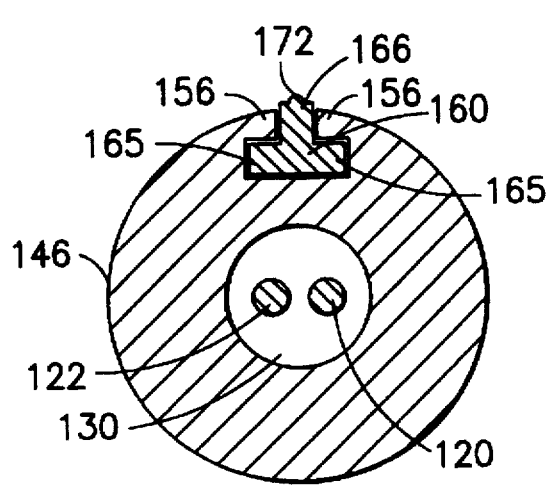
FIG. 6a is a cross-section taken along line 6a—6a in FIG. 5.
Figure 6B:
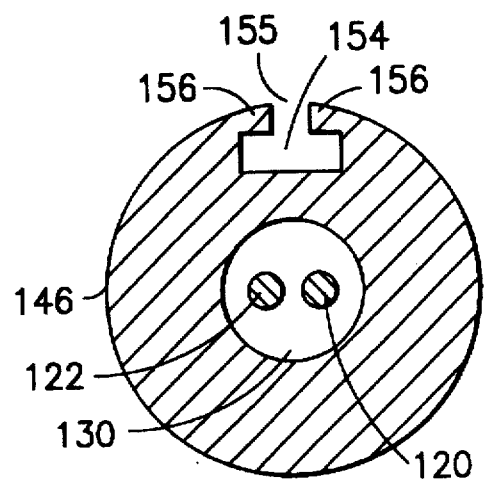
FIG. 6b is a view similar to FIG. 6a with the pick removed.
Figure 5:
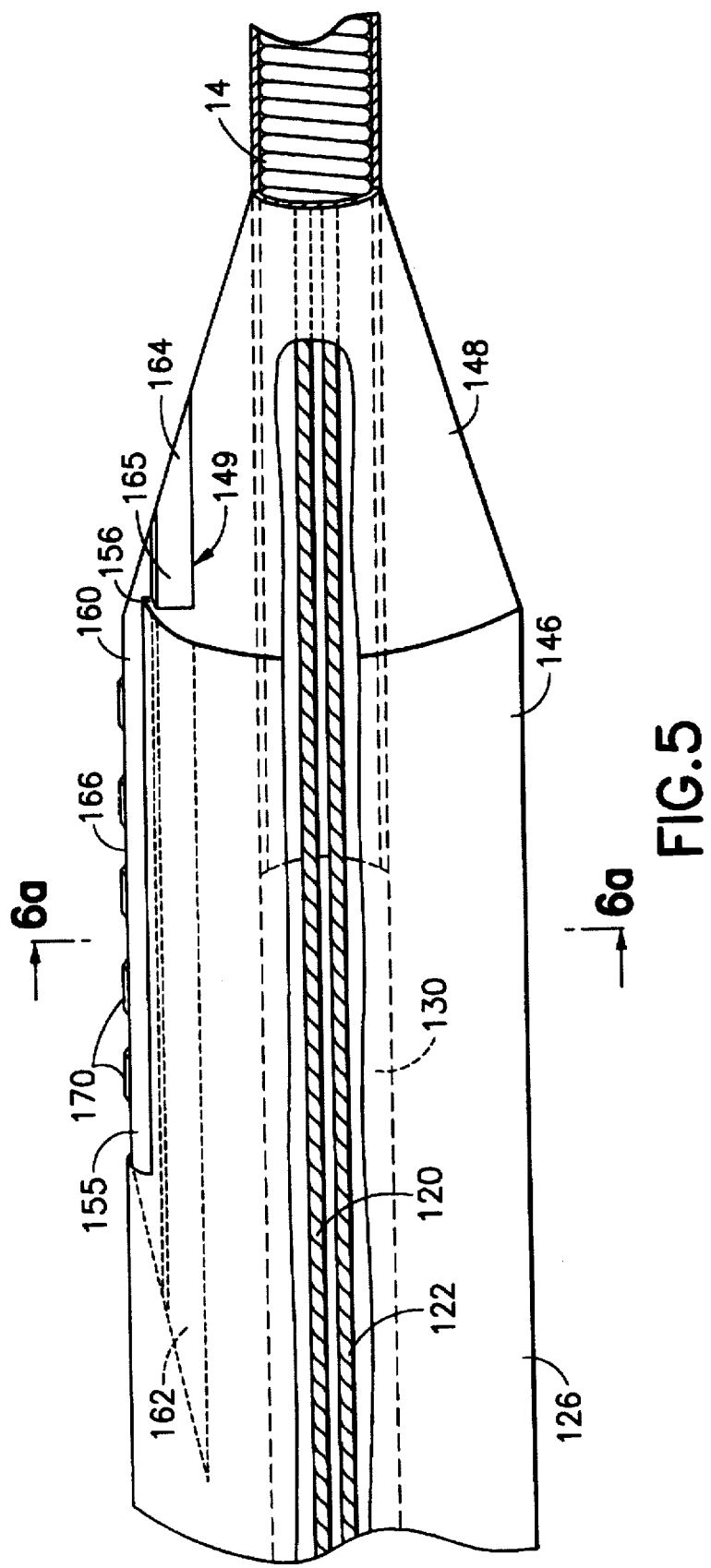
FIG. 5 is a view similar to FIG. 3 of a second embodiment of the invention.

Turning now to FIGS. 5 and 6b, a second embodiment of a handle having a removable pick is substantially similar to the first embodiment (with numbers incremented by 100 referring to like parts of the first embodiment). The handle includes a stationary member 126 having a pick holder 154 with a T-shaped profile defined by an open slot 155 and wing portions 156. The pick holder 154 has an entrance at a frustoconical portion 148 of the stationary member and extends proximally into a distal cylindrical portion 146 of the stationary member 126. The holder further includes an open slot 155 and wings 156. A pick 160, having a T-shaped cross-section, includes a proximal end 162, a distal arrow-shaped tip 164, sides 165, and a back 166. The pick 160 is slidably engaged in the holder 154 (FIG. 6a) with the open slot 155 exposing the back 166 of the pick and the wings 156 frictionally engaging the sides 165 of the pick. Alternatively, the sides 165 and back 166 of the pick 160 may frictionally engage the open slot 155 of the holder 154. The arrow-shaped distal tip 164 of the pick 160 preferably rests on a flattened portion 149 of the frustoconical portion 148 of the stationary member 126. The back 166 has several ridges 170 for finger engagement so that pressure may be applied to the ridges to overcome friction and slide the pick 160 out of the frustoconical portion 148 of the stationary member 126.

Figure 8A:
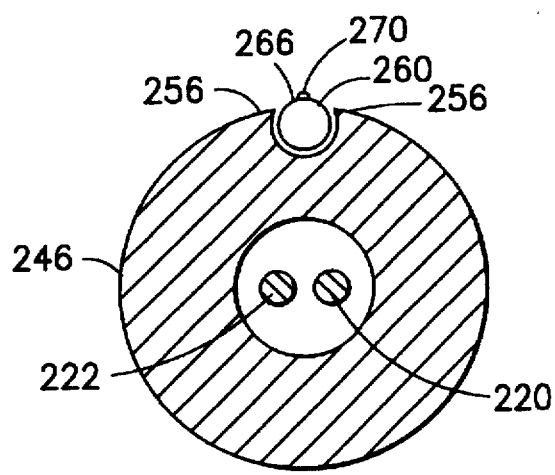
FIG. 8a is a cross-section taken along line 8a—8a in FIG. 7.
Figure 8B:
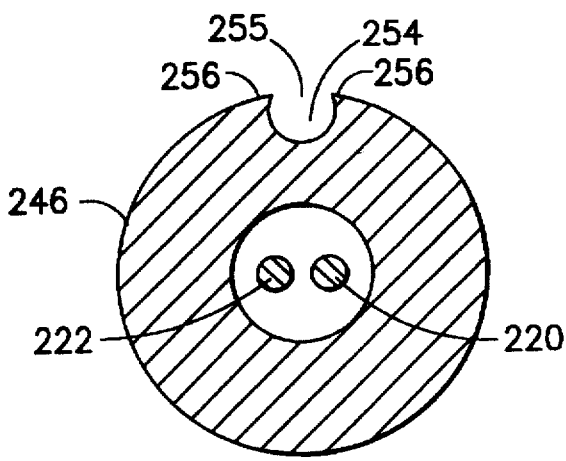
FIG. 8b is a view similar to FIG. 8a with the pick removed.

Referring to FIGS. 7 and 8b, a third embodiment of a handle assembly with removable pick (with numbers incremented by 200 referring to like parts of the first embodiment), includes a stationary member 226 having a tubular pick holder 254. The pick holder 254 has an entrance 261 at a frustoconical portion 248 of the stationary member and extends proximally into a distal portion 246 of the stationary member. A cylindrical pick 260, with a tapered proximal end 262, a distal end 264, and a back 266, is slidably and frictionally engaged in the holder 254 (FIG. 8a). The holder 254 has an open slot 255 which exposes the back 266 of the pick and wings 256 which frictionally engage the pick. The tapered proximal end 262 narrows to a point 268. The distal tip 264 of the pick is preferably supplied with a finger catch 272 (FIG. 7) engageable by a finger so that pressure may be applied to frictionally release the pick and slide the pick 260 out of the entrance at the frustoconical portion 248 of the stationary member 226. The back 266 is also preferably supplied with several ridges 270 for similarly releasing the pick.

Figure 10A:
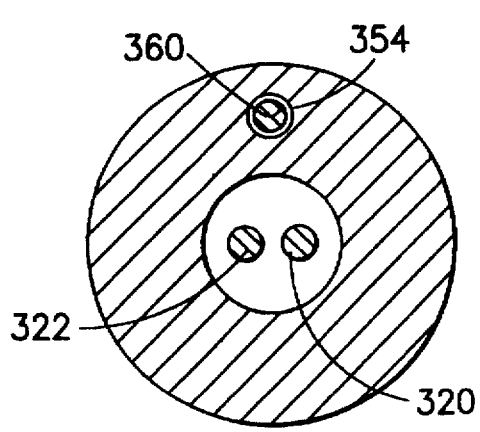
FIG. 10a is a cross-section taken along line 10a—10a in FIG. 9.
Figure 10B:
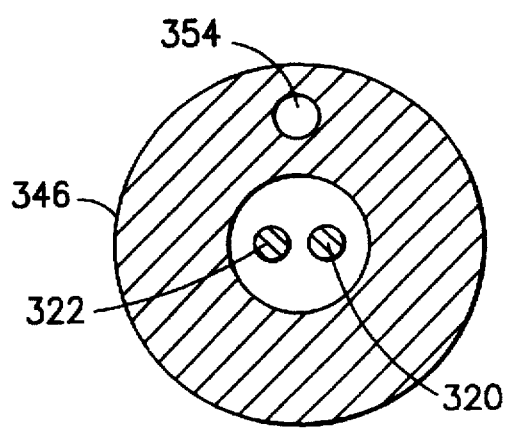
FIG. 10b is a view similar to FIG. 10a with the pick removed.
Figure 9:
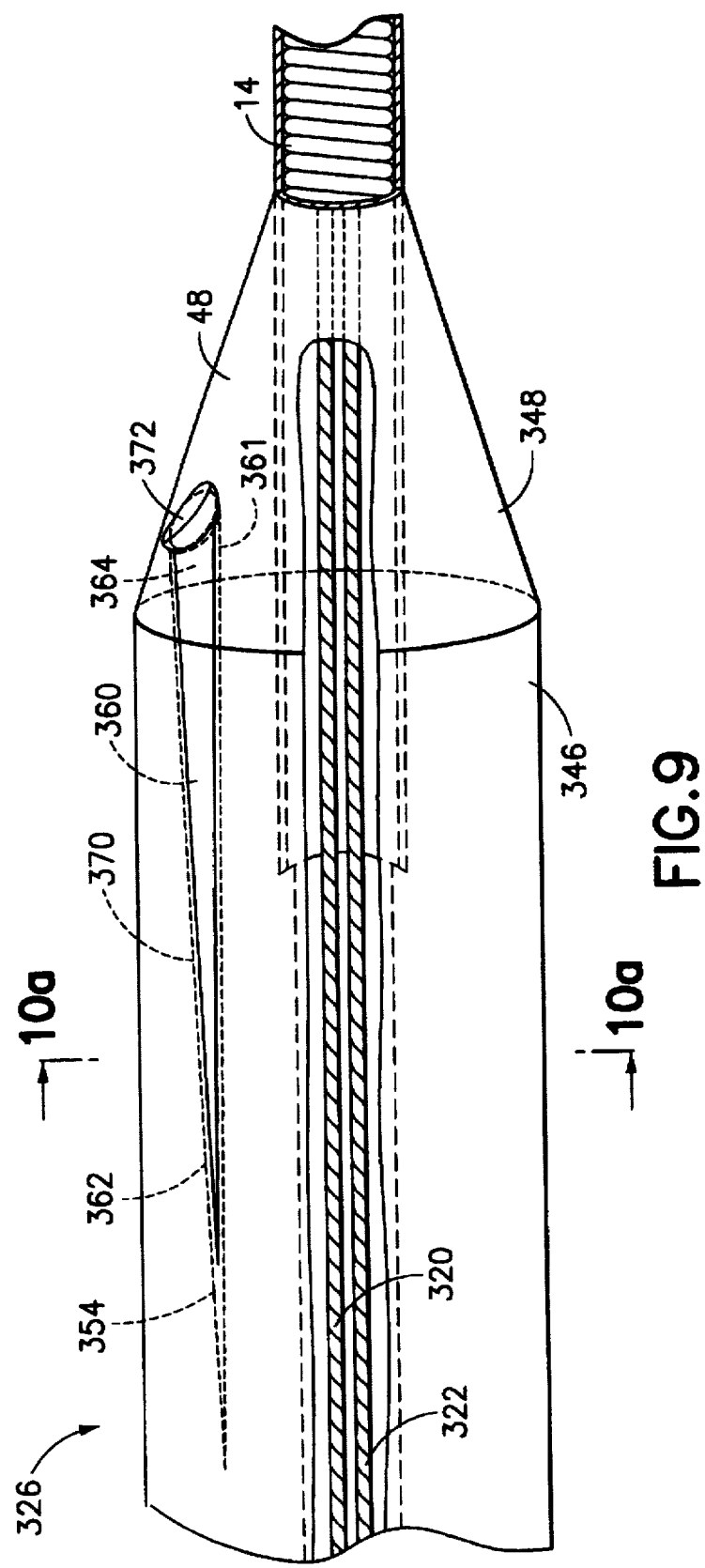
FIG. 9 is a view similar to FIG. 3 of a fourth embodiment of the invention.

Turning now to FIGS. 9 and 10b, a fourth embodiment is shown of a handle assembly with a removable pick, substantially similar to the first embodiment (with numbers incremented by 300 referring to like parts of the first embodiment). A stationary member 326 of the handle includes a tapered bore pick holder 354 having an entrance 361 at a frustoconical portion 348 of the stationary member 326 and extending proximally into a distal cylindrical portion 346 of the stationary member 326. A pick 360, tapered to a point 362 and having a manipulation end 364 is slidably and frictionally engaged with the wall 370 of the tapered bore holder 354 (FIG. 10a). The pick 360 extends out of the holder 354 and has a finger catch 372 at its manipulation end 364 for engagement by a human finger. The pick 360 is easily removed from the bore holder 354 by engaging the finger catch 372 with a finger and disengaging the pick form the holder 354.

It will be appreciated by those skilled in the art that the handle portion of an endoscopic biopsy forceps may take other forms besides one including a stationary member and a displaceable spool. Thus, as seen in FIG. 11, an endoscopic forceps instrument 410 according to another embodiment of the invention includes a proximal actuation handle 412, a flexible member or coil 414, and control wires 420, 422. The proximal actuation handle 412 includes a lever 424 pivotally coupled to a stationary member 422. The control wires 420, 422 extend through the coil 414 and the proximal ends of the control wires are coupled to a rack member 434 as described below.

The stationary member 422 has a lower finger ring 426 and an upper stepped throughbore 428. The stepped throughbore 428 has a larger diameter proximal portion 430 and a smaller diameter distal portion 432. A cylindrical rack member 434 is slidably disposed in the larger diameter portion 430. The rack member 434 has a plurality of cogs 438 spaced apart by defining grooves 437. The distal end of the rack member 434 is provided with a longitudinal bore 440 for receiving the control wires 420, 422. The lever 424 of the actuation handle 412 has a lower thumb ring 446 and an upper pinion portion 448. The lever 424 is pivotally coupled to the stationary member 422 by a pivot pin 450 and is arranged so that the upper pinion portion 448 enters the larger diameter portion 434 of the throughbore 428 through the lower slot opening 431 and engages the cogs 438 and grooves 437. The actuation handle is described in detail in previously incorporated U.S. Pat. No. 5,478,350.

The proximal end of the coil 414 is coupled to the smaller diameter portion 432 of the throughbore 428 in the stationary member 422. As described with reference to FIG. 2, the coil is coupled via a clevis to jaws and the control wires are coupled to the tangs 85, 86 of the jaws 80, 82. The end effector operates as described herein above and with respect to the co-owned U.S. Pat. No. 5,228,451 to Bales et al.

From the foregoing, those skilled in the art will appreciate that when the lever 424 is rotated about the pivot pin 450, the pinion portion 448 imparts a linear reciprocal motion to the rack member 434. As the rack member 434 is moved linearly, it will be appreciated that the rack member effects a translational movement of the control wires 420, 422 relative to the coil 414 and operates the end effectors.

Figure 12:
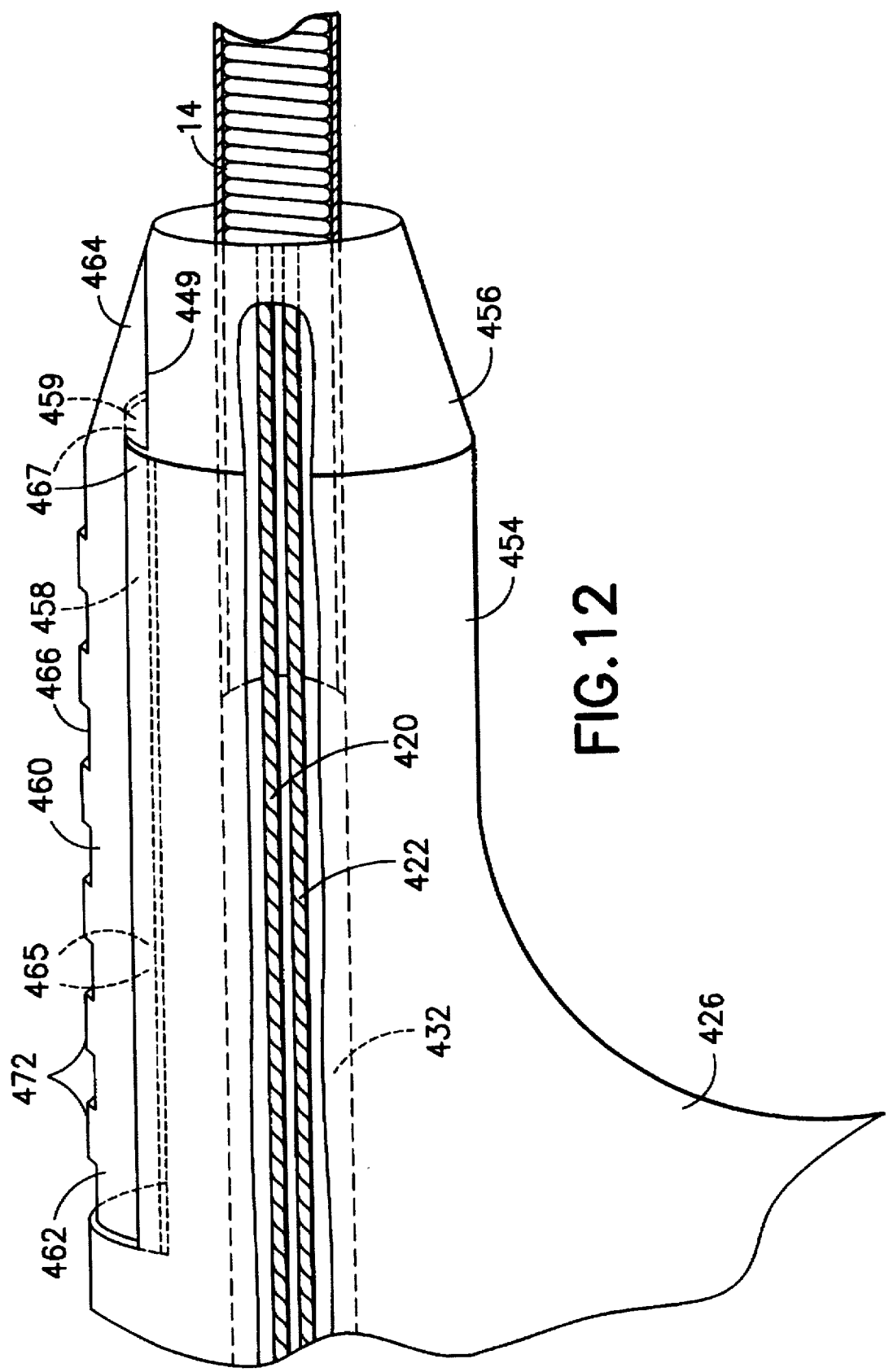
FIG. 12 is an enlarged broken side elevation view in partial section of the instrument of FIG. 11.

As shown in FIG. 12, the stationary member 426 further includes a substantially cylindrical distal portion 454 having a substantially frustoconical portion 456. With reference to FIGS. 11a and 12, a pick holder 458 is provided in the stationary member 426. The holder 458 is a cutout in the stationary member having an entrance at the frustoconical portion and extending proximally into the distal cylindrical portion 454. The holder is substantially trapezoidal in profile defined by an open slot portion 459 and wings 467. A pick 460 with a dovetail (or trapezoidal) cross-section has a proximal end 462, a distal arrow-shaped tip 464, sides 465, and a back 466. The pick is slidably and frictionally engaged in the holder 458 with the open slot 459 of the holder 458 exposing the back 466 of the pick, and the wings 467 frictionally engaging the sides 465 of the pick. The arrow-shaped distal tip 464 of the pick 460 preferably rests on a flattened portion 449 of the frustoconical portion 448 of the stationary member 426. The back 466 of the pick has several ridges 472 engageable by a finger to overcome friction and slide the pick 460 out of the stationary member 426.

It will be appreciated that any of the embodiments previously disclosed in reference to a surgical instrument having an actuation handle having a stationary member and displaceable spool can also be applied to the surgical instrument having an actuation handle having a stationary member and a lever.

Turning now to FIGS. 13 and 13a, a sixth embodiment is shown of a handle assembly with a removable pick, substantially similar to the second embodiment (with numbers incremented by 400 referring to like parts of the second embodiment). The handle includes a stationary member 526 having a plurality pick holders 554a, 554b, 554c, 554d. A plurality of picks 560a, 560b, 560c, 560d are slidably disposed within the pick holders.

It will be appreciated that a multiple pick holder having multiple picks permits the practitioner to have available extra picks in the event a first pick withdrawn from a holder is misplaced or contaminated in the interim of being withdrawn from the holder and used by the practitioner. Moreover, when an actuation handle having multiple pick holders and multiple picks is used in a multiple sample bioptome instrument, the practitioner has available a separate pick for removing each of several tissue samples from the jaw cups of the forceps, thereby preventing contamination across the samples.

It will be appreciated that the multiple pick holder and picks may take the shapes of any of the holders and picks of the preceding embodiments. In addition, while four pick holders and picks have been shown in FIGS. 13 and 13a, it will be appreciated that the stationary member of the sixth embodiment may have any number of pick holders and picks greater than one. Furthermore, while the picks and holders in the sixth embodiment have been shown to be equally radially spaced about the periphery of the stationary member, it will be appreciated that the pick holders and picks may otherwise be arranged.

There has been described and illustrated herein a flexible microsurgical instrument having a proximal handle portion which includes a holder for receiving a specimen pick and a specimen pick held therein. While preferred embodiments of the invention have been described, it is not intended that the invention be limited thereto, as it is intended that the invention be as broad in scope as the art will allow and that the specifications be read likewise. Thus, while the invention has been described with particular reference to endoscopic biopsy instruments having a coil, it will be appreciated that the inventive concepts disclosed herein can be advantageously applied to other types of surgical instruments. In addition, while the pick holder and pick have been described with respect to a variety of embodiments, it will be appreciated that other shaped holders and picks which allow a pick to slidably engage a holder can also be used. Also, while several ridges for a finger to engage have been shown on the back of some embodiments, it will be appreciated that other finger engageable structures, such as recessed notches, or no finger engageable structure can be used. Further, while the pick has been shown to have at least one end that narrows to a point, it will be appreciated that a point can be located at either end, at neither end, or at both ends. Moreover, while two distinct actuation handles have been shown, it will be understood that different types of actuating handles can be used to achieve substantially the same result in substantially the same manner, wherein the different actuation handles have a pick holder and a pick held therein. Additionally, while the control wires have been shown attached to the jaws of the jaw assembly, it will be understood that a single control wire which may be split at its distal end can also be used. It will therefore be appreciated by those skilled in the art that yet other modifications could be made to the provided invention without deviating from its spirit and scope as so claimed.

We claim:

1. An actuator handle assembly for an endoscopic biopsy forceps instrument having a tubular member, a control means extending through the tubular member, and a pair of forceps jaws coupled to the control means such that relative movement of the control means and the tubular member opens and closes the jaws, said actuator handle comprising:

(a) a stationary member having a distal end coupled to one of the control means and the tubular member, said stationary member having at least one holder means for receiving and holding a pick; and (b) a movable member coupled to the other of the control means and the tubular member and movable relative to said stationary member.

2. An actuator handle assembly according to claim 1, further comprising:

(c) at least one pick slidably engaged with said at least one holder means.

3. An actuator handle assembly according to claim 2, wherein:

said holder means is a groove in said stationary member.

4. An actuator handle assembly according to claim 3, wherein:

said pick has a trapezoidal cross-section and said groove has a trapezoidal profile.

5. An actuator handle assembly according to claim 3, wherein:

said pick has a T-shaped cross-section and said groove has a T-shaped profile.

6. An actuator handle assembly according to claim 2, wherein:

said pick is conical.

7. An actuator handle assembly according to claim 2, wherein:

said pick tapers.

8. An actuator handle assembly according to claim 2, wherein:

said pick is cylindrical and has a tapered end.

9. An actuator handle assembly according to claim 2, wherein:

said pick has a point at one end.

10. An actuator handle assembly according to claim 2, wherein:

said pick has a back side having a plurality of ridges.

11. An actuator handle assembly according to claim 2, wherein:

said pick is arrow-shaped.

12. An actuator handle assembly according to claim 11, wherein:

said stationary member comprises a cylindrical portion having a frustoconical portion at a distal end and wherein said frustoconical portion has a flattened portion such that said flattened portion has a triangular profile.

13. An actuator handle assembly according to claim 2, wherein:

said at least one holder means comprises a plurality of holder means, and said at least one pick comprises a plurality of picks.

14. An endoscopic instrument, comprising:

a) a tubular member;

b) a control means extending through said tubular member;

c) a pair of forceps jaws coupled to said tubular member and said control means, such that relative movement of said control means and said tubular member opens and closes the jaws; and d) an actuator handle, comprising i) a stationary member having a distal end coupled to one of said control means and said tubular member, said stationary member having at least one holder means for receiving and holding a pick, and ii) a movable member coupled to the other of said control means and said tubular member and movable relative to said stationary member.

15. An endoscopic instrument according to claim 14, further comprising:

e) at least one pick slidably engaged with said at least one holder means.

16. An endoscopic instrument according to claim 15, wherein:

said pick tapers.

17. An endoscopic instrument according to claim 15, wherein:

said pick has a point at one end.

18. An endoscopic instrument according to claim 15, wherein:

said pick has a back side having a plurality of ridges.

19. An endoscopic instrument according to claim 15, wherein:

said pick is arrow-shaped.

20. An endoscopic instrument according to claim 15, wherein:

said at least one holder means comprises a plurality of holder means, and said at least one pick comprises a plurality of picks.

* * * * *

UNITED STATES PATENT AND TRADEMARK OFFICE
CERTIFICATE OF CORRECTION

PATENT NO. : 5,722,422
DATED : Mar. 3, 1998
INVENTOR(S) : Palmer et al.

It is certified that error appears in the above-identified patent and that said Letters Patent is hereby corrected as shown below:

col. 5, line 29, delete "422" and insert -- 426 --.

col. 5, line 33, delete "422" and insert -- 426 --.

col. 5, line 33, delete "426" and insert -- 427 --.

col. 5, line 44, delete "422" and insert -- 426 --.

col. 5, line 53, delete "422" and insert -- 426 --.

Signed and Sealed this

Second Day of November, 1999

Attest:

Q. TODD DICKINSON

*Attesting Officer*   *Acting Commissioner of Patents and Trademarks*